United States Patent [19]

Ito

[11] 4,151,089
[45] Apr. 24, 1979

[54] DEVICE FOR HIGH EFFICIENCY CONTINUOUS COUNTERCURRENT EXTRACTION USING A ROTATING HELICAL TUBE

[75] Inventor: Yoichiro Ito, Bethesda, Md.

[73] Assignee: The United States of America as represented by the Secretary of the Department of Health, Education and Welfare, Washington, D.C.

[21] Appl. No.: 906,868

[22] Filed: May 17, 1978

[51] Int. Cl.² .............................................. B01D 15/08
[52] U.S. Cl. ............................... 210/198 C; 210/511
[58] Field of Search ................. 210/31 C, 198 C, 511; 55/197, 199

[56] References Cited

U.S. PATENT DOCUMENTS

| 2,029,690 | 2/1936 | Wilson | 210/511 X |
| 2,405,158 | 8/1946 | Mensing | 210/511 X |
| 3,775,309 | 11/1973 | Ito et al. | 210/31 C |
| 4,028,056 | 6/1977 | Snyder et al. | 210/198 C |
| 4,040,742 | 8/1977 | Ito et al. | 356/39 |
| 4,041,025 | 9/1977 | Ito | 210/31 C |
| 4,058,460 | 11/1977 | Ito | 210/198 C |

Primary Examiner—John Adee
Attorney, Agent, or Firm—Browdy and Neimark

[57] ABSTRACT

A continuous extraction system wherein two immiscible solvents move in opposite directions through a rotating helical column. Elution of a desired phase takes place by use of a separation device at the head end which selects either the heavier or the lighter phase. This may consist of a suitably weighted suspended outlet tube in a rotating cylindrical outlet chamber or may consist of a shunt and settling chamber located outside the rotating part; the heavier phase may be removed from the bottom and the lighter phase may be removed from the top.

13 Claims, 6 Drawing Figures

DEVICE FOR HIGH EFFICIENCY CONTINUOUS COUNTERCURRENT EXTRACTION USING A ROTATING HELICAL TUBE

FIELD OF THE INVENTION

This invention relates to continuous countercurrent devices for the separation of samples, and more particularly to an elution method and apparatus for continuous countercurrent chromatography of the type employing a rotating coiled tube, with gravimetric separation means cooperating with said rotating tube.

BACKGROUND OF THE INVENTION

Various arrangements for countercurrent chromatography have been developed to produce high efficiency solute partitioning in two-phase solvent systems. These systems generally use a stationary phase which is retained in the column while the mobile phase elutes through the system. In these prior systems, since the sample solution is introduced at the beginning of each operation, such systems are regarded as constituting batch separation techniques, and not continuous extraction processes.

However, continuous extraction processes necessitate "genuine" countercurrent flow, wherein two immiscible solvents move in opposite directions with respect to the separation column to allow continuous sample feeding and continuous enrichment and/or stripping of the ingredient or ingredients desired to be collected, present in a large quantity of liquid. Heretofore no satisfactory system for accomplishing this objective has been available.

The following prior U.S. Pat. Nos. illustrate the present state of the art:
Ito et al., 3,775,309
Ito et al., 4,040,742
Ito, 4,051,025
Ito, 4,058,460

SUMMARY OF THE INVENTION

In order to meet the above-described continuous-flow extraction requirement, the present invention employs the "genuine" countercurrent flow of two immiscible solvents through a helical column to achieve high-efficiency continuous solute extraction or partitioning. This extraction scheme will be useful not only in the separation of chemicals in research laboratories, but also in large-scale industrial applications, including reprocessing nuclear fuels and in eliminating hazardous pollutants from industrial waste water.

The principle employed is substantially as follows:

When an end-closed coiled tube containing two immiscible liquids is rotated in an acceleration field acting perpendicular to the axis of the coil, a dynamic equilibrium is established wherein the two liquids occupy approximately equal volumes in each coil unit from one end of the coil (the head end), and any excess of either phase remains at the other end of the coil (the tail end). This dynamic equilibrium of the two phases enables a high efficiency separation of solutes when the mobile phase is eluted through the head end of the coiled tube. Both retention of the stationary phase and thorough mixing of the phases are attained in the coiled tube so as to separate solutes according to their partition coefficients. For example, an efficiency of up to 10,000 theoretical plates has been achieved in the separation of dinitrophenyl amino acids using the flow-through coil planet centrifuge technique.

In order to introduce "genuine" countercurrent flow through this rotating coiled tube, it is further necessary to understand the following physical properties inherent in this dynamic equilibrium of two phases in the rotating coiled tube:

(1) It creates a linear pressure gradient from the head end to the tail end through the coiled tube. The maximum pressure difference $P_{max}$ can be calculated from the equation $$P_{max} = n\,(\rho_H - \rho_L)\,g\,h,$$

where n denotes the number of coil units; $\rho_L$ and $\rho_H$ denote the densities of the lighter and heavier phases; g denotes the acceleration; and h denotes the helical diameter. Thus, if the two portions of the coil containing the two phases are connected with a tube, the liquids start to circulate through the newly created loop in a direction from the head to the tail end through the connecting tube.

(2) When any amount of one phase is replaced by the other phase at any portion of the coil containing the two phases, the dynamic equilibrium is quickly reestablished by itself by "genuine" countercurrent flow of the two phases, i.e., forward movement of the former phase and backward movement of the latter phase.

(3) There are two directions for introducing the flow through the entire length of the coiled tube. The head-tail elution with either phase results in retention of the other phase in the coiled tube, as described above. On the other hand, the tail-head elution with either phase elutes out both phases until the entire column space is occupied by the same phase.

Accordingly, a main object of the present invention is to provide an improved countercurrent chromatography system which overcomes the deficiencies and disadvantages of the previously-used systems employed in countercurrent chromatography.

A further object of the invention is to provide a novel and improved system for high-efficiency solute partitioning which employs countercurrent flow wherein two immiscible solvents move in opposite directions with respect to a separation column to allow continuous sample feeding and continuous collection of a desired ingredient or ingredients.

A still further object of the invention is to provide an improved method and apparatus for continuous-flow countercurrent chromatography of the type employing a rotating coiled tube, wherein separation and collection are effected by cooperation of gravimetric separation means with the rotating coiled tube, and wherein the output flow may be selected to be either only the heavier phase or only the lighter phase of a two-phase mixture.

A still further object of the invention is to provide an improved continuous-flow countercurrent chromatography system which utilizes a rotating helical column to separate two phases of different densities and which further utilizes pressure gradients derived from the difference in densities to produce a circulation aiding in the selective output of one or the other of the two phases.

A still further object of the invention is to provide an improved continuous-flow countercurrent chromatography system which employs a rotating helical column in a gravity field to separate two phases of different densities, which collects the two phases in a chamber at the head end of the column, which allows the lighter and heavier phases to become separated in said chamber, and which includes means to elute one or the other of said two phases with high efficiency.

More general objects include providing for improved separation or extraction of components in a liquid; and providing a genuine countercurrent liquid-liquid separation process and apparatus.

BRIEF DESCRIPTION OF THE DRAWINGS

Further objects and advantages of the invention will become apparent from the following description and claims, and from the accompanying drawings, wherein:

DESCRIPTION OF PREFERRED EMBODIMENTS

On the basis of the above-described physical factors, there will now be considered the provision of "genuine" countercurrent flow through the rotating coiled chromatography tube.

Figure 1:
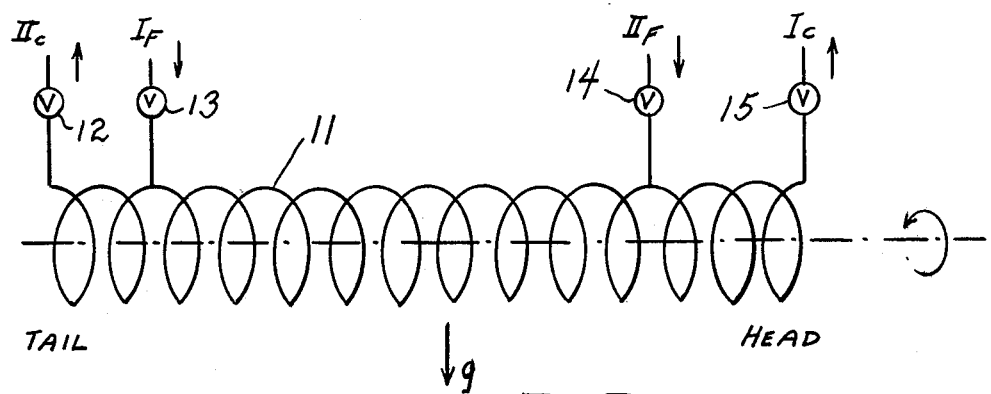
FIG. 1 is a diagrammatic representation of a horizontal rotating coiled chromatography tube in a gravitational field, with inlet and outlet flow tube connections for two immiscible phases.

Referring to the drawings, FIG. 1 shows a rotating helically coiled tube 11 in an acceleration (gravitation) field g. The coiled tube 11 has two pairs of flow-connecting tubes, $I_F$ and $I_C$ to respectively feed and collect phase I, and $II_F$ and $II_C$ to respectively feed and collect phase II, where phases I and II are two immiscible phases in the rotating coiled tube 11. These flow-connecting tubes may be brought outside the rotating parts of the apparatus in a conventional manner with or without the use of rotating seals, as will be presently discussed. The flow-connecting tubes may be provided with suitable control valves 12 to 15, as shown.

The flow-connecting tubes $II_C$ and $I_F$ are located at the tail end of coiled tube 11 and the flow-connecting tubes $II_F$ and $I_C$ are located at the head end.

Assume that the rotating coiled tube 11 contains phases I and II in a dynamic equilibrium state, with all valves 12 to 15 closed. It is then possible to introduce phase II through tube $II_F$ and collect the same phase through tube $II_C$ by opening valves 14 and 12 to establish countercurrent flow of phase II through the coiled tube 11. However, introduction of phase I through tube $I_F$ to collect this phase exclusively at $I_C$ is difficult because in this situation both phases will be eluted at tube $I_C$. This difficulty can be solved, however, by utilizing one of the following two possible methods:

1. Employ a selecting device at the head of the coiled tube 11 arranged such that only phase I is eluted through tube $I_C$.

2. Take out the mixture of phases I and II in such a way that the flow rate of phase I through tube $I_C$ is equal to the feed rate of phase I through tube $I_F$ while returning the eluted phase II into the coiled tube 11 through a loop established between tubes $I_C$ and $II_F$.

FIGS. 2 to 5 show examples of head end phase-selecting devices utilizing the first of the above two methods.

Figure 2:
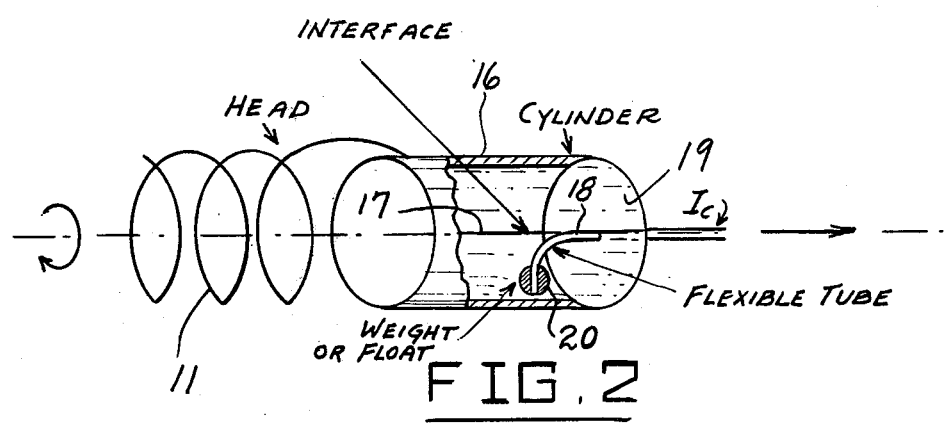
FIG. 2 is a diagrammatic view showing a structural arrangement according to the present invention connected to the head end of the chromatography tube of FIG. 1 for eluting a desired phase.
Figure 3:
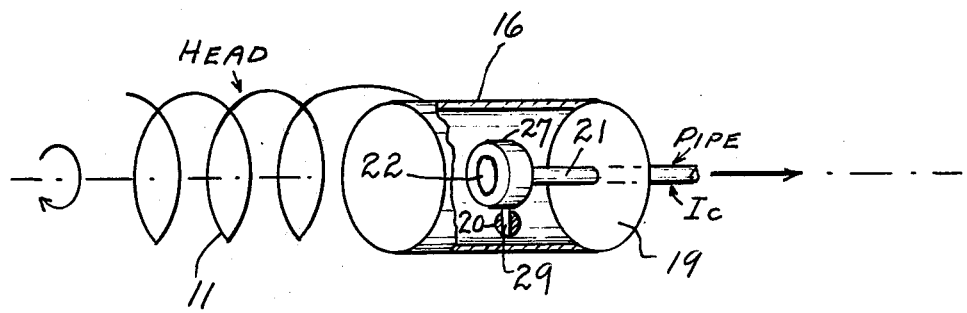
FIG. 3 is a diagrammatic view similar to FIG. 2 but showing a modification of the structural arrangement.

FIGS. 2 and 3 illustrate the use of a hollow cylinder 16 which is connected to the head end of the coiled tube 11 and is mounted to rotate coaxially therewith, whereby the acceleration g acts perpendicularly to the axis of the cylinder. Two-phase mixture introduced from the head of coiled tube 11 into the cylinder 16 can then be separated by the acceleration field into two phases, the heavier phase being at the bottom and the lighter phase being at the top, with an interface at 17, as shown in FIG. 2. These two phases remain substantially stationary relative to the acceleration field g, while the rotating cylinder moves relative to said two phases. Thus, if the input portion of collection tube $I_C$ stays always in the lower part of the cylinder 16, this permits only the heavier phase to be eluted, and if the input portion of collection tube $I_C$ stays always in the upper part of said cylinder, this permits only the lighter phase to be eluted through $I_C$.

The phase-selecting device of FIG. 2 comprises a flexible tube 18 extending rotatably and sealingly through the center of the circular end cylinder wall 19 and leading to collecting tube $I_C$. Flexible tube 18 has a weight (or float) 20 secured thereon close to its inner end. If the density of the element 20 is substantially greater than that of the heavier phase, it forces the inner end of tube 18 to be always positioned in the heavier phase, and if the density of element 20 is substantially less than that of the lighter phase, it acts as a float and forces the inner end of flexible tube 20 to stay always in the lighter phase. Thus, by suitable selection of the density of element 20, either the heavier or the lighter phase may be eluted at $I_C$.

Figure 4:
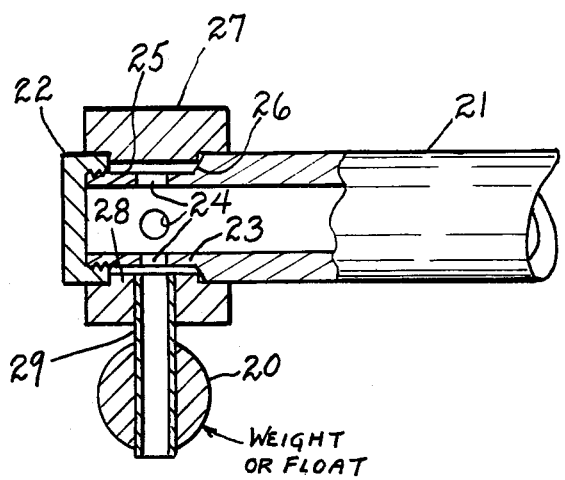
FIG. 4 is an enlarged vertical cross-sectional view taken longitudinally through the inner end portion of the elution pipe of FIG. 3.

FIGS. 3 and 4 show another embodiment similar to FIG. 2 wherein the eluting tube $I_C$ comprises a rigid pipe 21 extending rotatably and sealingly through the center of the cylinder end wall 19 and being provided with an end closure cap 22 threadedly engaged on a reduced end portion 23 of the pipe. Said reduced end portion is provided with a plurality of flow holes 24. An annular groove is thus defined between cap 22 and the shoulder 26 adjacent reduced portion 25. A ring member 27 is freely rotatably mounted on the pipe, said ring member having an inner annular retaining rib 28 which engages rotatably in said annular groove. The ring member is provided with a radial outlet tube 29 on which is mounted a weight (or float) 20 similar to that employed in FIG. 2. Thus, the ring member 27 can freely rotate around the pipe 21 as a bearing, while permitting flow from the outlet tube 29 through the perforations 24 in the reduced pipe portion 23. The proper selection of the density of the weight or float element 20 biases the outlet tube 29 downwardly or upwardly in the rotating cylinder 16 to permit elution of the desired phase into collection tube $I_C$.

Figure 5:
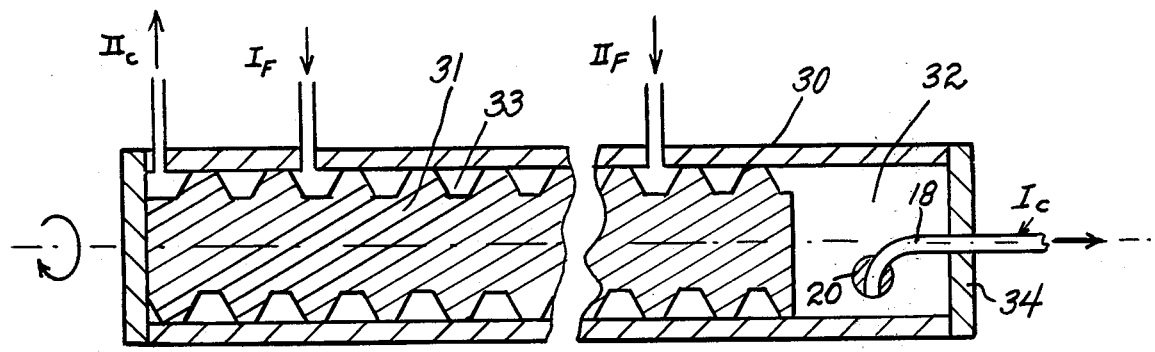
FIG. 5 is a longitudinal cross-sectional view of a further modification of a chromatography column and head end elution arrangement according to the present invention.

Another embodiment which is functionally generally similar to that of FIG. 2 is illustrated in FIG. 5, wherein the design of a coiled column with a cylinder is simplified by employing a cylindrical, elongated, precisionbore casing 30 in which is tightly secured a threaded rod 31 which is sufficiently shorter than the length of the casing so as to define a cylindrical space 32 at the head end of the helical column defined by the helical space 33 between the rod 31 and the inside surface of the casing 30. As in FIG. 2, a flexible tube 18 may be employed, extending rotatably and sealingly through the center of end wall 34 of casing 30, with a weight or float 20 secured on its inner end, to define the elution collection conduit $I_C$. Alternatively, the pipe 21, ring 27, radial tube 29, and weight or float 20 of FIGS. 3 and 4 may be employed in the embodiment of FIG. 5.

Figure 6:
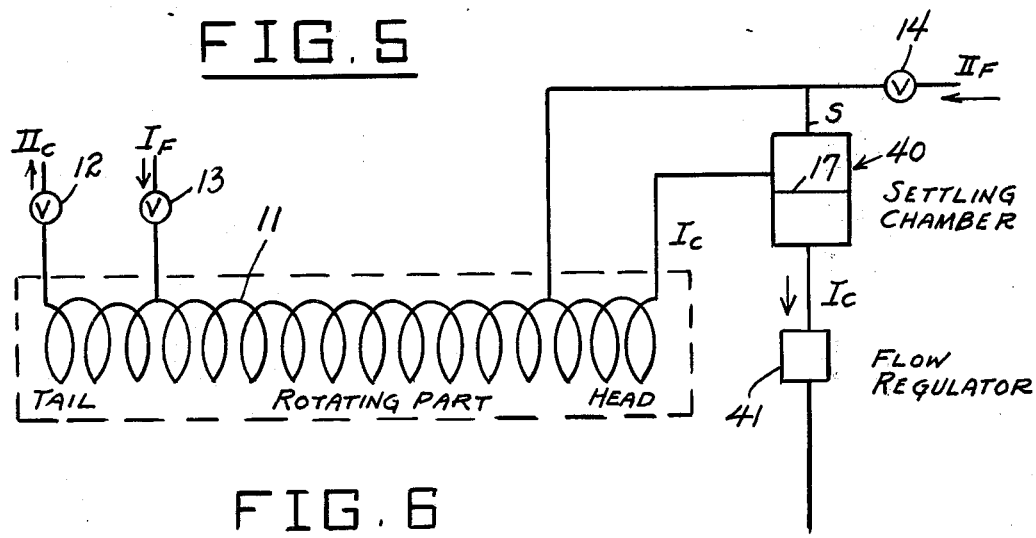
FIG. 6 is a diagrammatic view of a further modified structural arrangement according to the present invention, using a shunt and settling chamber outside the rotating part of the chromatography assembly.

FIG. 6 shows an embodiment which employs the second of the above-described possible methods, namely, which uses a shunt and settling chamber outside the rotating part. FIG. 6 shows the use of an arrangement which allows continuous countercurrent extraction by employing a shunt S between the flow tubes $I_C$ and $II_F$, and including a settling chamber 40. Phase mixture eluted through $I_C$ first enters the settling chamber 40, where phase separation takes place in the gravitational field. Phase I (in this case the heavier phase) is removed from the bottom of the settling chamber through a flow regulator 41 at a rate equal to the feed rate of phase I through $I_F$. (If phase I is the lighter phase it is removed from the top portion of the settling chamber rather than from the bottom). Then, in the case illustrated in FIG. 6, phase II (in this case the lighter phase) separated in the chamber 40 spontaneously enters S and $II_F$ to return into the coiled tube 11 due to the pressure difference between the points of connection of $II_F$ and $I_C$ to coiled tube 11, as previously described. Phase II pumped through $II_F$ is mixed with the same phase entering through S and then enters the coiled tube 11, where it splits into two streams, one flowing toward the tail of the coiled tube 11 and eluted through $II_C$ at the rate equal to the feed rate through $II_F$, and the other flowing toward the head end of the coiled tube 11 to circulate through the loop defined by settling chamber 40 and shunt element S.

In operation of the apparatus, the entire space of the coiled tube 11 is first filled with the extraction phase (phase II). Elimination of air bubbles from the coiled tube 11 can be completed by introducing the solvent from the tail into the rotating coiled tube. After closing the valve 12 at $II_C$, the sample phase (phase I) which contains solute or solutes to be extracted, is introduced through $I_F$, and a flow regulator employed on $I_C$ is adjusted to elute the solvent at the same rate. When phase I starts to elute through $I_C$, the extraction phase (phase II) is introduced through $II_F$ and the valve 12 on $II_C$ is opened to elute the same phase. When the optimal conditions of flow rates and rotational speed are chosen, a steady "genuine" countercurrent flow will soon be attained in the portion of the coiled tube between the inlets of $I_F$ and $II_F$.

Applicable flow rates of the two phases depend upon various factors such as:

(1) column factor (internal diameter, helical diameter and length of the tube), (2) apparatus factor (acceleration field and rotational speed, and (3) solvent factor (interfacial tension, viscosity, and density difference of the two phases), and should be determined by preliminary experiments.

Rotation of the coiled tube 11 with respect to the gravitational and/or centrifugal acceleration fields may be accomplished by conventional means, for example, as shown in U.S. Pat. Nos. 3,775,309, 4,051,025, and 4,058,460, above cited. All flow tubes of the rotating coiled tube 11 are brought to the outside of the rotary member of the apparatus either with or without the use of rotating seals. U.S. Pat. No. 3,775,309 shows an arrangement providing a rotating centrifugal force field without the use of rotating seals. U.S. Pat. No. 4,051,025 shows an arrangement including a slowly rotating coiled tube in the gravitational field. Although it requires two sets of rotating seals, it can be conveniently and economically adapted for large-scale industrial use. Likewise, the arrangement of U.S. Pat. No. 4,058,460 can utilize both gravitational and centrifugal acceleration field without the use of rotating seals. Therefore, it is suitable for both small-scale laboratory use and large-scale industrial applications.

While certain specific embodiments of continuous countercurrent devices for the separation of samples, using a rotating chromatography column, have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A flow-through countercurrent chromatography apparatus comprising means defining an axially rotatable helical column comprising a plurality of successive helical-chamber coil elements and having a head end and a tail end, first phase feed conduit means connected to said column at a coil element adjacent to but spaced from said tail end, second phase feed conduit means connected to said column at a coil element adjacent to but spaced from said head end, second phase collection conduit means connected to the tail end of the column, and first phase collection conduit means connected to the head end of the column, said first phase collection conduit means including gravimetric phase separation means for separating the phases in accordance with their densities, and output conduit means connected to said gravimetric phase separation means for eluting a selected separated phase from said gravimetric phase separation means.

2. The flow-through countercurrent chromatography apparatus of claim 1, and wherein said rotatable helical column is mounted substantially horizontally.

3. The flow-through countercurrent chromatography apparatus of claim 1, and wherein said gravimetric phase separation means comprises a chamber included in the flow circuit of said first phase collection conduit means for receiving the first and second phases and arranged to allow an interface to be gravimetrically established between said phases.

4. The flow-through countercurrent chromatography apparatus of claim 3, and means to communicatively connect said output conduit means to a selected interior level in said chamber relative to said interface.

5. The flow-through countercurrent chromatography apparatus of claim 4, and wherein said chamber has an end wall, and wherein said output conduit means is swivelly mounted in said end wall and has a laterally extending inlet portion.

6. The flow-through countercurrent chromatography apparatus of claim 5, and wherein said output conduit means is provided at said inlet portion with level-seeking means having a predetermined degree of buoyancy relative to the phases.

7. The flow-through countercurrent chromatography apparatus of claim 6, and wherein said output conduit means comprises a flexible tube.

8. The flow-through countercurrent chromatography apparatus of claim 6, and wherein said output conduit means comprises a rigid pipe and said inlet portion comprises a conduit element perpendicularly swivelled to said pipe.

9. The flow-through countercurrent chromatography apparatus of claim 6, and wherein said chamber is connected to the head end of said column and is mounted to rotate coaxially therewith.

10. The flow-through countercurrent chromatography apparatus of claim 9, and wherein said chamber is substantially cylindrical and said output conduit means is swivelly engaged through the center of said end wall.

11. The flow-through countercurrent chromatography apparatus of claim 1, and wherein said gravimetric phase separation means comprises a settling chamber included in the flow circuit of said first phase collection conduit means, and shunt conduit means connected so as to form a loop to return eluted second phase liquid from said settling chamber to said helical column.

12. The flow-through countercurrent chromatography apparatus of claim 1, and wherein said gravimetric phase separation means comprises a stationary settling chamber included in the flow circuit of said first phase collection conduit means, and shunt conduit means communicatively connecting said second phase feed conduit means to a location in said settling chamber such as to define a loop for returning eluted second phase liquid into the helical column.

13. A flow-through, countercurrent liquid-liquid extraction apparatus, comprising an axially rotatable helical passageway having a head end and a tail end, first phase feed means to continuously feed a first liquid phase to said passageway adjacent said tail end, second phase feed means to continuously feed a second liquid phase to said passageway adjacent said head end, first phase collection means to continuously collect said first liquid phase from said passageway adjacent said head end, second phase collection means to continuously collect said second liquid phase from said passageway adjacent said tail end, means to axially rotate said helical passageway and thereby create a centrifugal acceleration or gravitational field, and means to separate said first and second liquid phases according to their densities, for passage of said first liquid phase through said first phase collection means.

* * * * *